Figure 1:
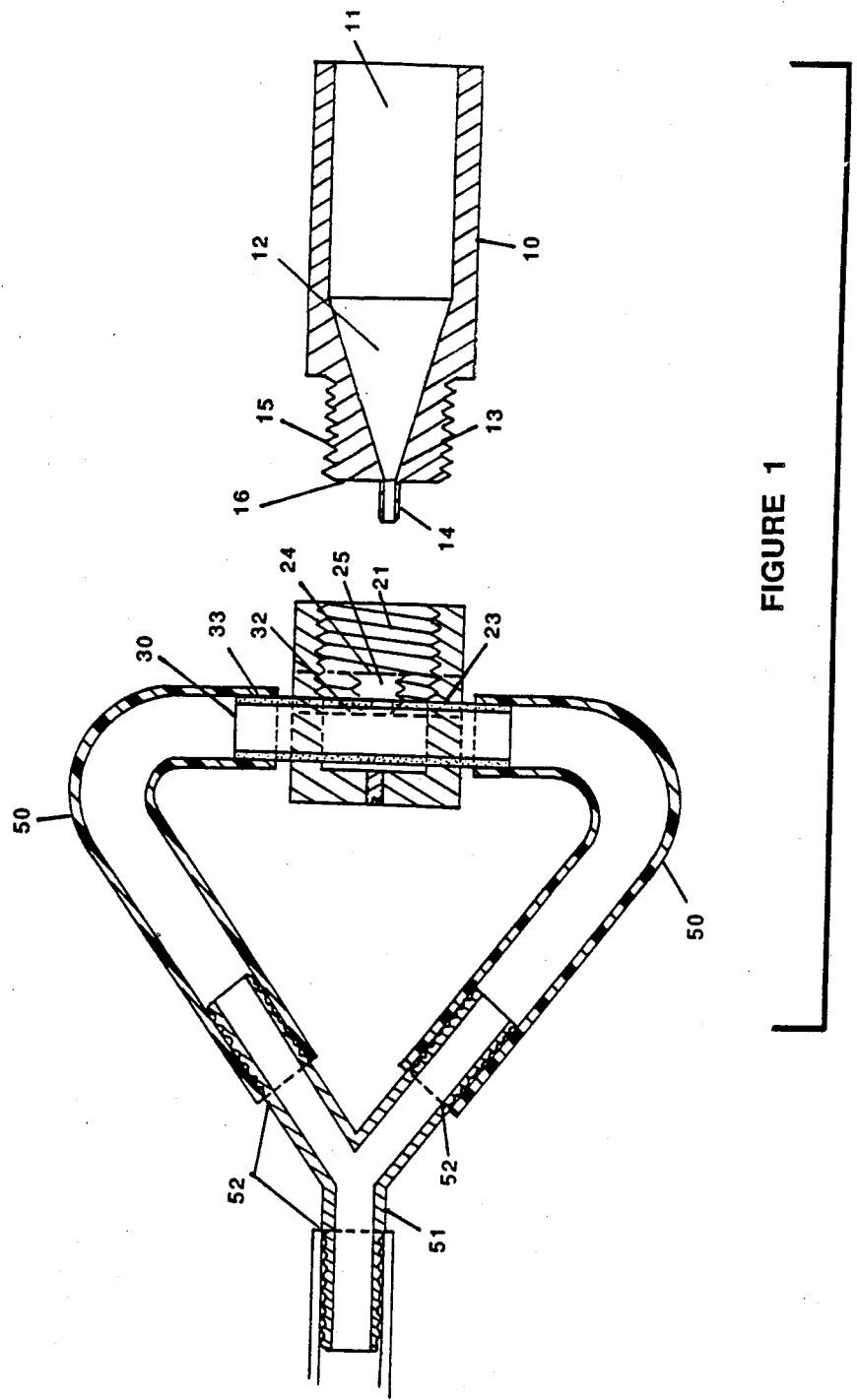
Figure 2:
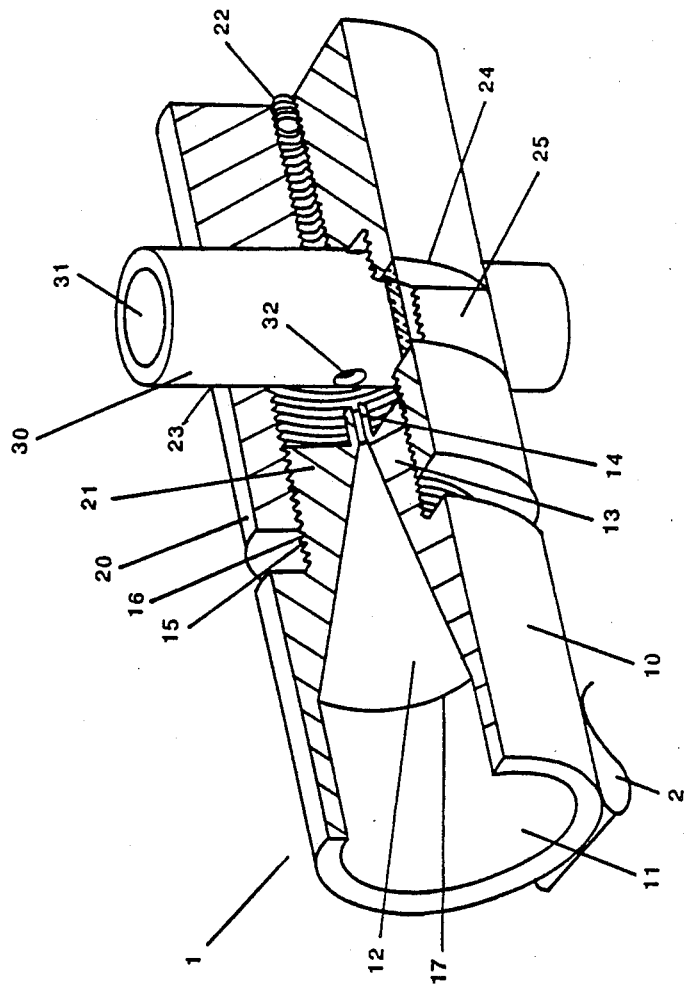
Figure 3:
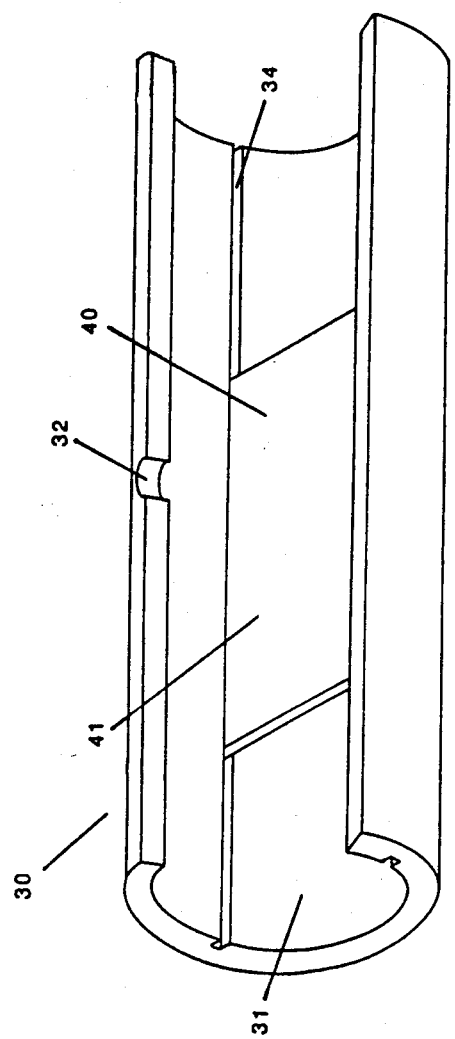

United States Patent [19]
Dewhurst

[11] Patent Number: 4,926,679
[45] Date of Patent: May 22, 1990

[54] INERTIAL IMPACTION AIR SAMPLING DEVICE

[76] Inventor: Katharine H. Dewhurst, 13150 Wenonah SE. Apt. 727, Albuquerque, N. Mex. 87123

[21] Appl. No.: 130,926

[22] Filed: Dec. 10, 1987

[51] Int. Cl.$^5$ ............................................. G01N 31/00
[52] U.S. Cl. ...................................... 73/28; 73/863.22
[58] Field of Search ........... 73/863.22, 863.21, 863.12, 73/28; 55/17, 270, 423, 462, 465

[56] References Cited

U.S. PATENT DOCUMENTS

| | | | |
|---|---|---|---|
| 2,538,116 | 1/1951 | May | 73/28 |
| 3,221,541 | 12/1965 | Osborne | 73/28 |
| 3,252,323 | 5/1966 | Turgeson | 73/863.22 |
| 3,677,650 | 7/1972 | Klangler | 55/270 |
| 3,970,428 | 7/1976 | Barringer | 73/863.22 |
| 3,975,946 | 8/1976 | Ball et al. | 73/864.84 |
| 4,144,032 | 3/1979 | Davis, Jr. | 73/863.21 |
| 4,178,794 | 12/1979 | Jugle et al. | 73/863.21 |
| 4,255,172 | 3/1981 | Smith | 73/28 |
| 4,350,037 | 9/1982 | Higham | 73/803.21 |

FOREIGN PATENT DOCUMENTS 578343 6/1933 Fed. Rep. of Germany .......... 73/28

OTHER PUBLICATIONS

Willeke et al., "Inclined-Surface Impaction for Respirable Particle Sampling", Atmospheric Environment, vol. 14, pp. 1109–1111 (1980).
Sneddon et al., "Direct Determination of Metals in Solid Samples", Plasma Es, no date.
Hwang, J., "Trace Metals in Atmospheric Particulates and Atomic Absorption Spectroscopy", *Analytical Chemistry*, vol. 44, No. 14, Dec. 1972, pp. 20A–27A.
Sneddon, J., "Direct Collection of Lead In The Atmosphere By Impaction For Determination by Electrolthermal Atomization Atomic Absorption Spectrometry", *Analytical Chemistry*, vol. 56, No. 11 Sep. 1984, pp. 1982–1986.

*Primary Examiner*—Stewart J. Levy
*Assistant Examiner*—Robert R. Raevis

[57] ABSTRACT

An inertial impactor to be used in an air sampling device for collection of respirable size particles in ambient air which may include a graphite furnace as the impaction substrate in a small-size, portable, direct analysis structure that gives immediate results and is totally self-contained allowing for remote and/or personal sampling. The graphite furnace collects suspended particles transported through the housing by means of the air flow system, and these particles may be analyzed for elements, quantitatively and qualitatively, by atomic absorption spectrophotometry.

21 Claims, 3 Drawing Sheets

INERTIAL IMPACTION AIR SAMPLING DEVICE

The United States Government has rights in this invention pursuant to Contract No. DE-AC04-76DP00789 between the Department of Energy and AT&T Technologies, Inc.

BACKGROUND OF THE INVENTION

The present invention relates generally to an inertial impaction air sampling device which is small-sized for portability and self-contained allowing for remote or personal sampling, and more particularly, to a portable, personal air sampling device capable of collecting respirable organometallic particulates in room environment air and direct analysis for providing immediate results.

The collection and analysis of elemental containing particulates, especially organometallic particulates in the presence of additional organic sample components, in ambient air is becoming increasingly important as maximum permissable exposure to toxic agents decreases. Accordingly, the relationship between the sampling method and the analytical method is becoming increasingly important. The particular analyte to be determined, as well as the particular sampling method chosen, will generally dictate the analytical procedure that can be used, and conventional sampling devices have not always proved satisfactory for providing the information desired.

Several air sampling devices are commonly known for collecting particulates in room air. Bulk or wipe samples do not yield useful information about airborne concentrations of contaminants. Filter sampling is not always reliable since filter loading can occur rapidly with membrane filters, and contaminants or oversized particles can be collected that would suggest higher than actual exposure. Also, no particle size distribution is obtainable without further analysis by electron microscopy or some other analytical technique. Further, filter samples generally require extensive treatment prior to the analysis, a process that is time consuming, expensive, and subjects the entire procedure to increased probability of errors.

Atomic absorption spectrometry offers advantages in the analysis of elemental containing particulates because it can provide low detection limits (more sensitive detection) and precise determinations for a wide variety of elements, and is thus very popular for non-real-time determinations. However, real time sampling would be optimum and would eliminate the potential problems associated with sample collection methods, sample transport, and sample preparation, and real time sampling has heretofore not been possible with atomic absorption spectrometry. Real time sampling would require, first, that an atomic absorption spectrometer be present in the vicinity of the sample being collected and, second, that multiple instruments be available should several sites be needed to be sampled simultaneously. This is neither economical or practical where the determination of occupational exposure must be made from a breathing zone sample, the "breathing zone" being commonly known as the space within one foot of the mouth and nose of the worker in an occupational environment.

Also, traditional atomic absorption methods utilize the sample in the form of a solution. Airborne particulates, however collected, must be subjected to a dissolution procedure, usually requiring acid digestion and a dilution process. These processes cause undesirable sample losses as do the pretreatment processes for filter sampling.

Additionally, specific methods for sampling and analysis using atomic absorption spectrophotometry have suffered from various specific disadvantages. Impinger samplers used with UV/VIS Absorption Spectrophotometry have been plagued with matrix interferences which preclude sensitive and precise detection of various organometallic elements, for instance hexaphenyl dilead in the presence of styrene. Filter collection methods used with Flame Atomic Absorption have been shown to have excessive loss of the sample. Because of the additional losses in the sample preparation for analysis, the overall efficiency of this method is less than 25% with poor precision.

The most precise and sensitive analytical method for sampling and detecting organometallic constituents in ambient air is inertial impaction sampling, a method which collects the sample in such a way that it can be deposited directly into the analytical measurement system, e.g. the spectrometer sample cell, combined with Graphite Furnace Atomic Absorption (GFAA) analysis. Compared with flame atomic absorption, this method of analysis offers low detection units, electrothermal atomization, more absorption, more sensitive detection—results using this method are approximately three orders of magnitude better than detection using flame atomic absorption—and the elimination of all sample pretreatment steps. However, in the past, inertial impaction has been limited to quantitative rather than qualitative analysis. Also, when inertial impaction samplers have been combined with graphite furnace impaction substrates, the furnace itself has been permanently mounted in the electrothermal atomization atomic absorption spectrometer, and a tapered collection device was inserted into the furnace for analysis. While this method is useful in the development of an area monitoring system for a workplace environment, it is not useful in the case of the determination of occupational exposure where samples must be collected in the breathing zone of the worker. Nevertheless, inertial impaction has been shown to be extremely efficient in the collection of respirable size particles (1–20 $\mu$m aerodynamic diameter), with entry losses in the range of 8–16% for particles from 1–7 $\mu$m aerodynamic diameter, and inertial impaction sampling plus GFAA analysis has proved to be the best sampling and analysis method for the determination of airborne organometallic particulates.

There is an existing need for a reliable and economical air sampling device to be used for both quantitative and qualitative analysis of materials in the environment.

Also, there is an existing need for an inertial impaction device designed as a personal breathing zone sampler, capable of size selective sampling of respirable size particles in the ambient environment (1–20 microns in diameter), low detection limits, and rapid, direct analysis without the need for extended sample preparation procedures.

There is a further need for a personal breathing zone sampler that is portable and attachable to an individual in the workplace, and that operates at a flow rate which closely approximates the rate of human respiration (2.0 L/min.).

There is still a further need for a personal breathing zone sampler device using a graphite furnace as the impaction substrate.

SUMMARY OF THE INVENTION

In view of the above-described needs, it is an object of this invention to provide a portable inertial impaction sampling device with remote capability which is capable of quantitative and qualitative analysis of solid aerosol particulates in gas efficiently and sensitively and capable of providing an impacted sample for analysis which is not removed from the substrate and requires no sample preparation process.

It is also an object of this invention to provide a portable inertial impaction sampling device which may be attached to an individual for providing a breathing zone sample.

It is another object of this invention to provide a portable inertial impact sampling device that may utilize a graphite furnace as the impaction substrate.

Additional objects, advantages, and novel features of this invention will become apparent to those skilled in the art upon examination of the following description or may be learned by the practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, there is provided a portable inertial impact sampler for detection and collection of solid aerosol particulates in gas, i.e. anything with mass suspended in a gas, including dust, vapor droplets, molecules or organometallic particulates. The sampler includes a cylindrical sample probe at one end for receiving, collimating, and expelling the gas flow, a tube arranged perpendicular to the expelling end of the probe and to the gas flow, a continuous sample collecting surface inside the perpendicular tube, and a removable mount for holding the probe and tube in a fixed position relative to each other during the collection of the sample. The mount may be adjusted for spacing the collection surface appropriately in relation to the end of the probe to allow for the collection of a particular size of particulate, because the size of particulate to be collected is controlled by this spacing, as well as the size of the end of the probe and the flow rate of the gas. The sampler arrangement according to the invention, where the tube containing the sampling surface is held in contact with the sample probe during collection and is removable for analysis, allows the direct size-selective collection of particles as an impacted sample that is not removed from the substrate for preparation, but may be analyzed according to the chosen method immediately and directly.

BRIEF DESCRIPTION OF THE DRAWINGS

The accompanying drawings, which are incorporated in and form part of the specification, illustrate an embodiment of the present invention and, together with the description, serve to explain the principles of the invention.

FIG. 1 is a plan view in cross-section of the disassembled portable inertial impact sampler.

FIG. 2 is a three-quarter section cutaway view of the assembled portable inertial impact sampler.

FIG. 3 is a cutaway view of a tube of the sampler structure in which a sample surface is held.

DETAILED DESCRIPTION OF THE INVENTION

As shown in the figures, one embodiment of the portable inertial impact sampler 1 includes a converging sample probe 10, mount 20, and tubular flow diverter 30, and a sample collector 40.

A preferred embodiment of inertial impact sampler 1 includes the use of a graphite tube as tubular diverter 30, the interior surface 31 of which is also sample collector 40. FIGS. 1 and 2 depict this preferred embodiment for the tubular diverter; in FIG. 1, tubular diverter 30 is shaded for clarity. Graphite tube 30 has a continuous inner surface 31 having a diameter of 6 millimeters for collection of the sample. The wall of tubular diverter 30 includes entry port 32 having a 2 millimeter diameter for introduction of the sample into the furnace. The size of the graphite tube or furnace is selected to be compatible with prior art devices for Graphite Furnace Atomic Absorption (GFAA) for single elemental analysis, or Inductively Coupled Plasma Atomic Emission (ICP) if a multi-elemental analysis is desired.

Although the preferred embodiment is described for an inertial impacter using a graphite furnace as the sample collector, persons reasonably skilled in the art will immediately recognize that alternative sample collectors with different dimensions are possible and may, under appropriate circumstances, be preferable. In fact, there are numerous possibilities for an impaction substrate to be utilized with the sampler of this invention; the material to be used for the substrate as well as the dimensions of the sampler structure may be chosen to fit the study to be performed and the analytical technique to be used.

For example, where xray fluorescence is the chosen method of analysis, the interior surface 31 of tubular diverter 30 will not be the sample collector as is the case with GFAA or ICP (which utilize the graphite furnace). In this case, as illustrated by FIG. 3, diverter 30 may be made of plastic, copper, or other suitable material with an interior surface structured to receive a removable plate sample collector 40 made of TEFLON (trademark), defined as Du Pont's tradename denoting all of its fluorocarbon resins, including PTFE, FEP, and various copolymers in *Whittington's Dictionary of Plastics*, Second Edition, Technomic Publishing Co., Inc., 1978, page 309, or other suitable, stable polymer or hydrocarbon material that is basically inert to the chemical process of the invention, which has a top surface 41 to directly receive the sample. For other types of analyses, silicon chips may be used as sample collecting surfaces.

FIG. 3 is a three-quarter cutaway view of the tubular diverter 30 containing a distinct sample collector 40 showing the use of support structure 34 in the interior wall 31 of tubular diverter 30. Preferably, in an arrangement where the sample collector 40 is a distinct structure from the tubular diverter 30, grooves will be used as support devices 34 for a sample collecting plate 40. Again, persons of reasonable skill in the art will recognize that may support devices other than grooves may be used according to the scope of the invention.

Referring again to FIGS. 1 and 2, probe 10 includes a cylindrical input end 11 of diameter D1 for receiving the flow of gas, and an interior surface 12. This cylindrical input end 11 increases inlet efficiency by significantly reducing turbulence in and around the vicinity of the inlet. Diameter D1 of the input end extends as the diameter of the interior surface 12 from input end 11 to a point 17 at one-half the length of probe 10 from input end 11 to an output end 13. At point 17, halfway down the length of probe 10, interior surface 12 tapers at an angle of approximately 55°-65° from the axis to output end 13, preferably at about 60°. This particular angle is important to this invention as it has been found to provide the optimum collection of particles by minimizing the effects of particle bounce from tapered surface 12, thus minimizing entry losses. Output end 13 preferably includes a jet 14 having a length-to-width ratio of 3 or greater, which collimates the flow of gas and particles into a stream along the axis of collector 10. This length-to-width ratio of jet 14 is important as it has been found to achieve laminar flow at 3 or greater. The tip of jet 14 is directed towards, and may be inserted into, port 32 for allowing the gas flow to contact sample collecting surface 40.

Mount 20 includes an open end 21 for being connected to the output end 13 of probe 10, which may be threaded to secure the connection; the connecting point between probe 10 and mount 20 is preferably vacuum sealed against the environment by some appropriate means, such as Teflon or a suitable polymer tape. A transverse cylindrical bore 23 centrally disposed and extending completely through mount 20 perpendicular to its axis and located just prior to the closed end 22. Tubular diverter 30 is inserted into and removed from mount 20 through bore 23. The connection between open end 21 and output end 13 allows for adjusting the spacing between sample collecting surface 40 and output end 13 to effect collection of a chosen size of particulate. Mount 20 also includes window opening 24 in one wall opposite and aligned with bore 23 to allow the inserted tubular diverter 30 to be viewed for observation and orientation with output end 13 of probe 10. This is particularly helpful when jet 14 is to be inserted into entry port 32. Window opening 24 is preferably vacuum sealed by some appropriate covering 25, such as glass. Mount 20 further includes a flat set screw 26 in closed end 22 to hold tubular diverter 30 in a fixed position.

Tubing 50 is connected to each end of the diverter tube 40 and extends outside sampler 1. The two sections of tubing 50 are connected with T-connector 51 and air flow through the tube is regulated with a personal sampling pump. This pump is not shown, but it may preferably be a vacuum pump attached to the individual where the breathing zone sample is being tested.

The connections 33 between the diverter tube 30 and the tubing 50 and connections 52 between the tubing 50 and the T-connector 51 are vacuum sealed with some appropriate means, such as with TEFLON(trademark) or or a suitable synthetic resin polymer tape, and may also be threaded to effect the connection.

Finally, FIG. 2 also shows a clip 2, connected to the exterior surface of input end 11 of probe 10, by which the sampler 1 may be attached to an individual for collecting an ambient air sample.

The basic operation of the invention is now apparent. In accordance with the preferred embodiment of the invention, the sampler 1 is attached by clip 2 to an individual for taking a breathing zone sample. Air flow is generated through tubes 50 which are attached to a vacuum pump on a belt pack of the individual wearing the sampler. Vacuum pump and belt pack are not shown but are standard items; the vacuum pump is typically a Gilian pump at a standardized flow rate. Air is pulled into inlet end 11 of probe 10 at a flow rate of 2 L/min., corresponding to the breathing rate of a human being. The flow is tapered in interior surface 12 and passes through jet 14 into tubular diverter 30 by entry port 32 to contact sample collector 40. Air flow then changes direction and passes out of each end of tubular diverter 30 through tubes 50, leaving an impacted, concentrated sample on the collector 40 which may be immediately analyzed without further sample preparation. In the case of the preferred embodiment, where a graphite tube or furnace in tubular diverter 30, the method used for immediate analysis is either Graphite Furnace Atomic Absorption for single elemental analysis, or Inductively Coupled Plasma Atomic Emission for a multi-elemental analysis.

Materials used in the sampler 1 may be aluminum for probe 10, typically QQ-A-225/8 Aluminum or 6061-P651 Aluminum, and brass or "half-hard" brass for mount 20, typically Type C 36000 ASTMB-16 halfhard brass. It is contemplated that future assemblies may use a great variety of materials. In one embodiment, the length of probe 10 is approximately 75 mm and the diameter is 41 mm. Jet 14 is 1.1 millimeter in diameter and is 4 millimeters in length. A 6 millimeter distance is allowed between the exit of jet 14 and the exterior wall of tubular diverter 30 for the preferred embodiment where a graphite tube is used for tubular diverter 30 as well as sample collector 40. The graphite tube itself is commercially available from Perkin-Elmer, with a 6 millimeter inner diameter and a 2 millimeter hole in its wall to be used as an entry port. Where a platform or plate 40 is used inside tubular diverter 30 to collect the sample, the distance between jet 14 and tubular diverter 30 is 3.5 millimeters. Tubing 50 through the air flow passes is typically TYGON(trademark), defined as a tradename for a series of vinyl compounds used as linings, coatings, adhesives, tubing and extruded shapes for chemical process equipment as corrosion protection, in Hawley's *The Condensed Chemical Dictionary*, Tenth Edition, Van Nostrand Reinhold Company, 1981, page 1065, with a ¼ inch inner diameter.

A prototype of this invention has been constructed and tested for performance. Using the parameters described above, test results showed that the sampler according to the invention allows size selective sampling of respirable size particles of 1–20 microns in diameter; using the preferred embodiment with the graphite furnace, results showed the invention to be approximately six orders of magnitude more sensitive for lead analysis than filter sampling that has typically been used. Prior to this invention, the current detection limit has only been 1 $\mu g/m^3$ at best. This increased sensitivity is primarily due to the rapid analysis time allowed because extended sample preparation procedures are eliminated, as well as to the decrease in sample loss afforded by the use of the invention because of the basic design of the sampler, again, the elimination of inherently lossy sample preparation procedures, and the use of the metal as the sample collector which dissipates the static charge on the charged particles. Previous sampling techniques using plastic devices get a increased sample loss due to migration of the particles.

Other advantages, not previously discussed, include the small portable nature of the invention, which allows the sample collector itself to be sent through the mail for analysis, and which also affords the device the versatility to be used as a process sampler, a personal sampler and an environmental sampler. Not least among the advantages is its practicality and economy: the jet 14 of the invention may be of any material, rather than tantalum which is expensive but was previously required for jets used for this purpose so the equipment could withstand the 4000° heat of the absorption spectrometer; and the graphite tube of the preferred embodiment no longer has to be discarded after analysis but can be cleaned and reused after the burnout that occurs during the analysis, thus bringing the cost of this sampling method into the range of gas badges or charcoal tube sampling.

The particular sizes and equipment discussed above are cited merely to illustrate particular embodiments of the invention. It is contemplated that use of this invention may involve components having different sensitivities and sizes as long as the principle described herein is followed. An inertial impaction sampler, constructed in accordance with the present invention, will provide accurate, reliable quantitative and qualitative sampling of solid aerosol particulates in gas with unusual speed, low detection limits, and versatility. It is intended that the scope of the invention be defined by the claims appended hereto.

I claim:

1. A portable inertial impact sampler of solid aerosol particulates in gas, comprising:

a. cylindrical means for collimating a flow of gas, said means having an input end for receiving the gas and an output end for expelling the gas, said output end being shaped to provide a parallel flow of gas in a first direction;

b. tubular flow diverting means for diverting said parallel gas flow to a second direction normal to said first direction;

c. a sample collecting surface within said flow diverting means; and d. mounting means, capable of being connected to said cylindrical means, for selectively (1) adjustably spacing said surface to receive said parallel flow from said output end, said surface extending parallel to said second direction, whereby the size of particulates collected on said surface is controlled by the size of said output end, the rate of flow of said gas, and the spacing between said output end and said surface; and (2) releasing said surface from said output end for measurement and analysis of particulates collected on said surface, said mounting means comprising a central axis, opposed first and second ends, said first end capable of being removably attached to said cylindrical means, a transverse cylindrical bore located at said second end of, and extending through said mounting means perpendicular to said central axis, whereby said tubular flow diverting means is capable of being removably inserted and rigidly fixed into said bore for collection of solid aerosol particulates in a gas, and a window aperture located in a wall of said mounting means opposite, but aligned with, said bore, whereby said tubular flow diverting means, when inserted into said bore, may be viewed for alignment with said output end of said cylindrical means.

2. A portable inertial air sampler, as claimed in claim 1, wherein the connecting point between said cylindrical means and said mounting means is sealed against the environment.

3. A portable inertial air sampler, as claimed in claim 1, wherein said cylindrical means comprises a cylindrical channel, tapering at about a 55°–65° angle from a point intermediate said input end and said output end to said output end.

4. A portable inertial air sampler, as claimed in claim 3, wherein said channel tapers at about a 60° angle from a point intermediate said input end and said output end to said output end.

5. A portable inertial air sampler, as claimed in claim 1, wherein said cylindrical means comprises a channel extending to a tubular jet at said output end of said cylindrical means, said jet being shaped for contacting said sample collecting surface with said gas flow.

6. A portable inertial air sampler, as claimed in claim 5, wherein said jet has a length-to-width ratio of 3 or greater.

7. A portable inertial impact sampler, as claimed in claim 1, further comprising means for attaching said cylindrical means, tubular flow diverting means, sample collecting surface, and mounting means to the lapel of an individual for sampling air in a personal breathing zone.

8. A portable inertial impact sampler, as claimed in claim 7, wherein said means for attaching comprises a clip.

9. A portable inertial impact sampler, as claimed in claim 1, wherein said tubular flow diverting means comprises a tube having an interior channel and opposed first and second ends, said first and second ends capable of being attached to an air flow device for effecting movement of air through said portable inertial air sampler, and a port in the wall of said tube located intermediate said first and second ends thereof, through which said gas flow enters said diverting means from said cylindrical means.

10. A portable inertial impact sampler, as claimed in claim 9, further comprising first, second, and third tubes and a T-connector, said first and second tubes connecting to said first and second ends respectively of said tubular flow diverting means and extending to said T-connector and said third tube capable of being attached to said air flow device.

11. A portable inertial impact sampler, as claimed in claim 10, wherein the connecting points of said first and second tubes to said first and second ends of said diverting means are vacuum sealed against the environment.

12. A portable inertial impact sampler, as claimed in claim 9, wherein said interior channel of said tubular flow diverting means comprises said sample collecting surface, whereby particles of said sample are collected on said interior channel of said tubular flow diverting means.

13. A portable inertial impact sampler, as claimed in claim 9, wherein said interior channel of said tubular flow diverting means includes oppositely disposed support means extending longitudinally through said channel and said sample collecting surface comprises a plate capable of being removably inserted into said interior channel to be supported by said support means.

14. A portable inertial impact sampler, as claimed in claim 13, wherein said support means comprise grooves.

15. A portable inertial impact sampler, as claimed in claim 1, wherein said window aperture is sealed against the ambient environment.

16. A portable inertial impact sampler, as claimed in claim 1, wherein said tubular flow diverting means consists of
- a graphite furnace, having an interior channel, wherein said entire interior channel comprises said sample collecting surface,
- opposed first and second ends, said first and second ends capable of being attached to an air flow device for effecting movement of air through said portable inertial air sampler, and
- a port in the wall of said tube located intermediate said first and second ends thereof, through which said gas flow enters said diverting means from said cylindrical means, whereby a particulate sample is collected by inertial impaction on said sample collecting surface of said graphite furnace and said sample is capable of immediate spectrographic analysis within said graphite furnace without further sample preparation.

17. A portable inertial impact sampler, as claimed in claim 16, wherein said analysis of said sample is graphite furnace atomic absorption.

18. A portable inertial impact sampler, as claimed in claim 16, wherein said analysis of said sample is inductively coupled plasma atomic emission.

19. A portable inertial impact sampler of solid aerosol particulates in gas, comprising:
  a. cylindrical means for collimating a flow of gas, said means having an input end for receiving the gas and an output end for expelling the gas, said output end being shaped to provide a parallel flow of gas in a first direction;
  b. tubular flow diverting means for diverting said parallel gas flow to a second direction normal to said first direction, consisting of
    - a graphite furnace, having an interior channel, wherein said entire interior channel comprises said sample collecting surface,
    - opposed first and second ends, said first and second ends capable of being attached to an air flow device for effecting movement of air through said portable inertial air sampler, and
    - a port in the wall of said tube located intermediate said first and second ends thereof, through which said gas flow enters said diverting means from said cylindrical means, whereby a particulate sample is collected by inertial impaction on said sample collecting surface of said graphite furnace and said sample is capable of immediate spectrographic analysis within said graphite furnace without further sample preparation; and
  c. mounting means, capable of being connected to said cylindrical means, for selectively
    (1) spacing said surface to receive said parallel flow from said output end, said surface extending parallel to said second direction, whereby the size of particulates collected on said surface is controlled by the size of said output end, the rate of flow of said gas, and the spacing between said output end and said surface; and
    (2) releasing said surface from said output end for measurement and analysis of particulates collected on said surface, said mounting means comprising
    - a central axis,
    - opposed first and second ends, said first end capable of being removably attached to said cylindrical means,
    - a transverse cylindrical bore located at said second end of, and extending through said mounting means perpendicular to said central axis, whereby said tubular flow diverting means is capable of being removably inserted and rigidly fixed into said bore for collection of solid aerosol particulates in a gas, and
    - a window aperture located in a wall of said mounting means opposite, but aligned with, said bore, whereby said tubular flow diverting means, when inserted into said bore, may be viewed for alignment with said output end of said cylindrical means.

20. A portable inertial impact sampler, as claimed in claim 19, wherein said analysis of said sample is graphite furnace atomic absorption.

21. A portable inertial impact sampler, as claimed in claim 19, wherein said analysis of said sample is inductively coupled plasma atomic emission.

* * * * *

UNITED STATES PATENT AND TRADEMARK OFFICE
CERTIFICATE OF CORRECTION

PATENT NO. : 4,926,679

DATED : May 22, 1990

INVENTOR(S) : Katharine H. Dewhurst

It is certified that error appears in the above-identified patent and that said Letters Patent is hereby corrected as shown below:

Title page, column 2, after "Assistant Examiner- Robert R. Raevis", and before "[57]   ABSTRACT", insert -- Attorney, Agent, or Firm - Anne D. Daniel; James H. Chafin; Judson R. Hightower--.

Signed and Sealed this

Seventeenth Day of March, 1992

Attest:

HARRY F. MANBECK, JR.

*Attesting Officer*

*Commissioner of Patents and Trademarks*